(12) United States Patent
Bowley et al.

(10) Patent No.: US 11,617,638 B2
(45) Date of Patent: Apr. 4, 2023

(54) IMPLANTABLE PROSTHESIS FOR SOFT TISSUE REPAIR

(71) Applicant: C.R. Bard, Inc., Murray Hill, NJ (US)

(72) Inventors: Melissa Bowley, Newport, RI (US); Devang Vijay Shah, Franklin, MA (US); Philip A. Tessier, Cranston, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 756 days.

(21) Appl. No.: 16/663,290

(22) Filed: Oct. 24, 2019

(65) Prior Publication Data

US 2020/0054431 A1 Feb. 20, 2020

Related U.S. Application Data (62) Division of application No. 15/539,423, filed as application No. PCT/US2014/072370 on Dec. 24, 2014, now Pat. No. 10,478,281.

(51) Int. Cl.
*A61F 2/00* (2006.01)
(52) U.S. Cl.
CPC .......... *A61F 2/0063* (2013.01); *A61F 2/0077* (2013.01); *A61F 2210/0076* (2013.01);
(Continued)
(58) Field of Classification Search
CPC ........ A61F 2/00; A61F 2/0063; A61F 2/0077; A61F 2/02; A61F 2/105; A61F 2230/0076; A61F 2230/0008; A61F 2210/0076
See application file for complete search history.

(56) References Cited

U.S. PATENT DOCUMENTS

| 2,671,444 A | 9/1954 | Pease, Jr. |
| 3,286,713 A | 11/1966 | Kurtz et al. |

(Continued)

FOREIGN PATENT DOCUMENTS

| EP | 0 719 527 A1 | 3/1996 |
| EP | 0 898 944 A2 | 3/1998 |

(Continued)

OTHER PUBLICATIONS

US 5,318,559 A, 07/1994, Mulhauser et al. (withdrawn)
(Continued)

*Primary Examiner* — Vi X Nguyen
(74) *Attorney, Agent, or Firm* — Wolf, Greenfield & Sacks, P.C.

(57) ABSTRACT

An implantable prosthesis for mending anatomical defects, including a groin hernia. The prosthesis includes a prosthetic repair patch that may be implanted in different tissue planes to mend a defect. The patch may include a medial portion configured to be positioned in a first tissue plane and a lateral portion configured to be positioned in a second tissue plane offset from the first tissue plane. The patch may include a transition region configured to extend through tissue and/or muscle, such as fascia, separating the tissue planes and transition the patch from one tissue plane to the other tissue plane. The transition region may be configured to inhibit buckling and/or bunching of the patch when implanted through the fascia. The lateral portion of the patch may have a level of stiffness that facilitates implantation of the patch in different tissue planes while inhibiting patient sensation to the implanted patch.

13 Claims, 5 Drawing Sheets

(52) U.S. Cl.
CPC .............. *A61F 2230/0008* (2013.01); *A61F 2230/0076* (2013.01); *A61F 2240/008* (2013.01)

(56) References Cited

U.S. PATENT DOCUMENTS

| | | |
|---|---|---|
| 5,122,155 A | 6/1992 | Eberbach |
| 5,258,000 A | 2/1993 | Gianturco |
| 5,249,682 A | 5/1993 | Transue |
| 5,219,077 A | 6/1993 | Transue |
| 5,254,133 A | 10/1993 | Seid |
| 5,366,460 A | 11/1994 | Eberbach |
| 5,368,602 A | 11/1994 | de la Torre |
| 5,397,331 A | 3/1995 | Himpens et al. |
| 5,634,931 A | 3/1997 | Kugel |
| 5,697,978 A | 12/1997 | Sgro |
| 5,766,246 A | 1/1998 | Mulhauser et al. |
| 5,769,864 A | 1/1998 | Kugel |
| 5,716,409 A | 10/1998 | Debbas |
| 5,824,082 A | 10/1998 | Brown |
| 5,916,225 A | 6/1999 | Kugel |
| 5,922,026 A | 7/1999 | Chin |
| D416,327 S | 9/1999 | Kugel |
| 5,879,366 A | 9/1999 | Shaw et al. |
| 5,954,767 A | 9/1999 | Pajotin et al. |
| 5,972,007 A | 10/1999 | Sheffield et al. |
| 5,990,378 A | 11/1999 | Ellis |
| 6,066,776 A | 5/2000 | Goodwin et al. |
| 6,113,623 A | 5/2000 | Sgro |
| 6,080,182 A | 6/2000 | Shaw et al. |
| 6,090,116 A | 7/2000 | D'Aversa et al. |
| 6,166,286 A | 12/2000 | Trabucco |
| 6,174,320 B1 | 1/2001 | Kugel et al. |
| 6,176,863 B1 | 1/2001 | Kugel et al. |
| 6,224,616 B1 | 1/2001 | Kugel |
| 6,241,768 B1 | 5/2001 | Agarwal et al. |
| 6,280,453 B1 | 8/2001 | Kugel et al. |
| 6,171,329 B1 | 9/2001 | Shaw et al. |
| 6,290,708 B1 | 9/2001 | Kugel et al. |
| 6,214,020 B1 | 10/2001 | Mulhauser et al. |
| 6,258,124 B1 | 10/2001 | Darois et al. |
| 6,383,201 B1 | 7/2002 | Dong |
| 6,551,356 B2 | 4/2003 | Rousseau |
| 6,565,580 B1 | 5/2003 | Beretta |
| 6,596,002 B2 | 7/2003 | Therin et al. |
| 6,610,006 B1 | 8/2003 | Amid et al. |
| 6,623,508 B2 | 9/2003 | Shaw et al. |
| 6,652,595 B1 | 11/2003 | Nicolo |
| 6,669,735 B1 | 12/2003 | Pelissier |
| 6,736,823 B2 | 5/2004 | Darois et al. |
| 6,800,082 B2 | 5/2004 | Rousseau |
| 6,790,213 B2 | 9/2004 | Cherok et al. |
| 6,926,723 B1 | 9/2005 | Mulhauser et al. |
| 7,011,688 B2 | 3/2006 | Gryska et al. |
| 7,101,381 B2 | 5/2006 | Ford et al. |
| 7,094,261 B2 | 8/2006 | Zotti et al. |
| 7,381,225 B2 | 3/2008 | Croce et al. |
| 7,824,420 B2 | 2/2010 | Eldridge et al. |
| 7,806,905 B2 | 5/2010 | Ford et al. |
| 7,785,334 B2 | 8/2010 | Ford et al. |
| 7,828,854 B2 | 9/2010 | Rousseau et al. |
| 8,123,817 B2 | 2/2012 | Intoccia et al. |
| 8,182,545 B2 | 5/2012 | Cherok et al. |
| 8,298,290 B2 | 10/2012 | Pélissier et al. |
| 8,388,633 B2 | 5/2013 | Rousseau et al. |
| 8,435,307 B2 | 7/2013 | Paul |
| 8,591,534 B2 | 11/2013 | Rousseau et al. |
| 8,579,924 B2 | 12/2013 | Stopek et al. |
| 2001/0049538 A1 | 6/2001 | Trabucco |
| 2002/0052654 A1 | 2/2002 | Darois et al. |
| 2002/0103494 A1 | 8/2002 | Pacey |
| 2002/0042658 A1 | 11/2002 | Tyagi |
| 2003/0130745 A1* | 7/2003 | Cherok ............... A61F 2/0063 623/23.72 |
| 2003/0171823 A1 | 11/2003 | Zotti et al. |
| 2004/0181288 A1 | 9/2004 | Darois et al. |
| 2004/0215219 A1 | 10/2004 | Eldridge et al. |
| 2005/0192600 A1 | 1/2005 | Nicolo |
| 2006/0064175 A1* | 3/2006 | Pelissier ............... A61F 2/0063 623/23.72 |
| 2006/0253203 A1 | 9/2006 | Alvarado |
| 2007/0225804 A1 | 9/2007 | Checa Ayet |
| 2007/0265710 A1 | 11/2007 | Brown et al. |
| 2007/0299538 A1 | 12/2007 | Roeber |
| 2008/0243149 A1 | 2/2008 | Kockerling et al. |
| 2008/0147099 A1 | 6/2008 | Uen |
| 2008/0033461 A1 | 7/2008 | Koeckerling et al. |
| 2009/0270999 A1 | 10/2009 | Brown |
| 2009/0069826 A1 | 12/2009 | Walther et al. |
| 2011/0190795 A1 | 4/2011 | Hotter et al. |
| 2011/0172786 A1 | 7/2011 | Rousseau et al. |
| 2011/0184441 A1 | 7/2011 | St-Germain |
| 2011/0208217 A1 | 8/2011 | Checa Ayet |
| 2011/0288567 A1 | 11/2011 | Ranucci et al. |
| 2012/0016186 A1 | 1/2012 | Cosson et al. |
| 2012/0179175 A1 | 12/2012 | Hammell |
| 2013/0158677 A1 | 6/2013 | Rousseau et al. |
| 2014/0012395 A1 | 9/2014 | Soares Da Costa et al. |
| 2017/0348084 A1 | 12/2017 | Bowley et al. |

FOREIGN PATENT DOCUMENTS

| | | |
|---|---|---|
| EP | 0 827 724 A3 | 11/1998 |
| EP | 1 674 048 A1 | 6/2006 |
| EP | 2 281 529 A1 | 2/2011 |
| FR | 2 744 906 A1 | 8/1997 |
| GB | 1 406 271 | 9/1975 |
| JP | 2008-513137 A | 5/2008 |
| JP | 2009-536550 A | 10/2009 |
| WO | WO 96/14805 A1 | 5/1996 |
| WO | WO 99/56664 A1 | 11/1999 |
| WO | WO 2006/034117 A1 | 3/2006 |
| WO | WO 2009/050890 A1 | 4/2009 |
| WO | WO 2012/040193 A1 | 3/2012 |
| WO | WO 2013/007534 A1 | 1/2013 |
| WO | WO 2013/048272 A1 | 4/2013 |
| WO | WO 2013/142353 A1 | 9/2013 |

OTHER PUBLICATIONS

International Serach Report and Written Opinion for International Application No. PCT/US2014/072370, dated Jun. 3, 2015, 17 pages.

International Preliminary Report on Patentability for International Application No. PCT/US2014/072370, dated Jul. 6, 2017, 9 pages.

Extended European Search Report for European Application No. 14909255.3, dated Jul. 9, 2018.

Fitzgibbons, Jr., Surgery Roundtable: Current Issues in Inguinal Herniorrhaphy. http://medscape.org/viewarticle/416375_3, 2 pages [last accessed Dec. 11, 2013].

Fitzgibbons, Jr. et al., Hernias of the Abdominal Wall. May 31, 2009. http://gustrength.com/health:hernias-abdominal-wall, 13 pages [last accessed Dec. 11, 2013].

Lourenço et al., The ONSTEP Inguinal Hernia Repair Technique: Initial Clinical Experience of 693 Patients, in Two Institutions. Hernia. 2013;17:357-64.

[No Author Listed] California Hernial Specialists. Hernia Types—Umbilical. http://www.californiaherniaspecialists.com/types-umbilical.html, 5 pages [last accessed Dec. 11, 2013].

[No Author Listed] Introducing the Ventralex™ ST Hernia Patch. Davol, Inc. http://davol.com/products/soft-tissue-reconstruction/hernia-repair/ventral-hernia-repair/umbilical-repair-options/ventralex-st-hernia-patch/, 2 pages [last accessed Dec. 11, 2013].

[No Author Listed] Maingot's Abdominal Operations Chapter 5: Hernias. http://www.uptomed.ir/digimed.ir/maingot-abdonimal-operation/maingot_abdominal_operation/II.%20abdominal%20wall/5.%20Hernias.htm, 71 pages. [last accessed Dec. 11, 2013].

Extended European Search Report dated Jul. 7, 2022, in connection with European Application No. 22164708.4.

(56) References Cited

OTHER PUBLICATIONS

U.S. Appl. No. 16/663,281, filed Oct. 24, 2019, Bowley.
EP 22164708.4, Jul. 7, 2022, Extended European Search Report.

* cited by examiner

IMPLANTABLE PROSTHESIS FOR SOFT TISSUE REPAIR

RELATED APPLICATIONS

This application is a divisional of U.S. patent application Ser. No. 15/539,423, filed Jun. 23, 2017, which is a national stage filing under 35 U.S.C. § 371 of International Patent Application No. PCT/US2014/072370, filed Dec. 24, 2014. The entire contents of these applications are incorporated herein by reference in their entirety.

FIELD

The present invention relates to an implantable prosthesis, and more particularly, to a prosthesis for mending a defect in a soft tissue or muscle wall.

BACKGROUND

Groin hernias are typically characterized as indirect inguinal hernias, direct inguinal hernias, and femoral hernias. It is known to repair such hernias by covering the defect with a prosthetic repair patch. In the classic 'Lichtenstein' procedure, the patch is placed anteriorly of the transversalis fascia. Alternatively, the patch may be positioned posteriorly of the transversalis fascia, for example, in the preperitoneal space between the transversalis fascia and the peritoneum.

A prosthetic repair patch may be delivered laparoscopically to the preperitoneal space in a procedure known as TEP—"Totally Extra Peritoneal". Alternatively, a prosthetic repair patch may be placed in the preperitoneal space via an 'open' procedure.

Two common open procedures for preperitoneal placement of a prosthetic repair patch include the POLYSOFT Hernia Patch procedure and the Kugel procedure. In the POLYSOFT approach, access to the preperitoneal space is through the defect itself. In the Kugel procedure, an opening is formed directly through the three layers overlying the preperitoneal space—the external oblique aponeurosis, the internal oblique aponeurosis, and the transversalis fascia. In both the POLYSOFT procedure and the Kugel procedure, the prosthetic repair patch is positioned in a single tissue plane between the peritoneum and the transversalis fascia.

Another open procedure for mending a groin hernia is the ONSTEP procedure which involves placement of a prosthetic repair patch in two different tissue planes. A medial portion of the patch is placed in the preperitoneal space and a lateral portion of the patch is placed in a tissue plane anteriorly of the transversalis fascia with a segment of the patch extending through the transversalis fascia.

It is an object of the present invention to provide a prosthesis for mending defects in soft tissue and muscle walls.

SUMMARY OF INVENTION

The present invention relates to an implantable prosthesis for mending an anatomical defect, such as a tissue or muscle wall defect, including a groin defect.

In one embodiment, an implantable prosthesis is provided for mending a groin hernia. The implantable prosthesis comprises a patch of repair fabric including a medial portion, a lateral portion and a transition region, and a support member located along the medial portion, the lateral portion and the transition region to help deploy and/or hold the patch in a spread out configuration. The medial portion is configured to be positioned at a first tissue plane, the lateral portion is configured to be positioned at a second tissue plane offset from the first tissue plane, and the transition region is configured to be positioned through tissue and/or muscle separating the first and second tissue planes. The support member includes a transition segment associated with the transition region of the patch. The transition segment is located from at least 2.5 cm to at least 5.1 cm from the lateral end of the patch and has an outer width that does not exceed 4.2 cm.

In another embodiment, an implantable prosthesis is provided for mending a groin hernia. The implantable prosthesis comprises a patch of repair fabric including a medial portion and a lateral portion. The medial portion is configured to be positioned at a first tissue plane, and the lateral portion is configured to be positioned at a second tissue plane offset from the first tissue plane and separated by tissue and/or muscle. The lateral portion has a stiffness of 0.04 psi to 0.09 psi.

In a further embodiment, a method is provided for mending a groin hernia. The method comprising acts of providing an implantable prosthesis and implanting the prosthesis to mend the groin hernia. The prosthesis includes a patch of repair fabric and a support member to help deploy and/or hold the patch in a spread out configuration. The patch includes a medial portion, a lateral portion and a transition region, and the support member is located along the medial portion, the lateral portion and the transition region. The support member includes a transition segment associated with the transition region. The prosthesis is implanted by positioning the medial portion of the patch at a first tissue plane, positioning the lateral portion of the patch at a second tissue plane offset from the first tissue plane, and positioning the transition region of the patch through an opening in tissue and/or muscle separating the first and second tissue planes. The transition segment of the support member has an outer width that does not exceed a corresponding dimension of the opening.

The foregoing is a non-limiting summary of the invention, which is defined by the attached claims. Other aspects, embodiments and/or features will become apparent from the following description.

BRIEF DESCRIPTION OF DRAWINGS

Various embodiments of the invention will now be described, by way of example, with reference to the accompanying drawings, in which.

DETAILED DESCRIPTION

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. It should be appreciated, then, that the various concepts and embodiments discussed herein may be implemented in any of numerous ways, as the disclosed concepts and embodiments are not limited to any particular manner of implementation. In addition, it should be understood that aspects of the invention may be used alone or in any suitable combination with other aspects of the invention.

The invention is directed to an implantable prosthesis for mending an anatomical defect, and is particularly suitable for mending defects in, and weaknesses of, soft tissue and muscle walls or other anatomical regions. The phrase "mending a defect" includes acts of repairing, augmenting, and/or reconstructing a defect and/or a potential defect. For ease of understanding, and without limiting the scope of the invention, the prosthesis is described below particularly in connection with mending a groin defect including, but not limited to, one or more of an indirect inguinal hernia, a direct inguinal hernia, a femoral hernia and/or other weakness or rupture of the groin anatomy. It should be understood, however, that the prosthesis is not so limited and may be employed in other anatomical procedures, as should be apparent to one of skill in the art.

The invention is more particularly directed to a prosthesis, such as a prosthetic repair patch, that may be implanted in different tissue planes to mend a defect. The patch may include a repair fabric having a body portion that is configured to be positioned in at least two offset tissue planes. For example, and without limitation, the patch may include a medial portion that is configured to be positioned in a first tissue plane and a lateral portion that is configured to be positioned in a second tissue plane that is offset from the first tissue plane. The patch may also include a transition region that is configured to extend through tissue and/or muscle separating the tissue planes and transition the patch from one tissue plane to the other tissue plane. The transition region may extend along and be part of the lateral portion and/or the medial portion, although the transition region may be a distinct portion of the patch located between the lateral and medial portions. Upon implantation of the patch, a segment of the patch associated with the transition region is to be positioned within the tissue and/or muscle. The specific segment will depend on the position of the implanted patch within the anatomy.

In one embodiment, the prosthesis may be configured to mend a groin hernia, including direct and indirect hernias. For such a repair, the medial portion may be configured for placement in a preperitoneal space, such as the space of Retzius. The lateral portion may be configured for placement in a separate tissue plane, such as anteriorly of the transversalis fascia, in an onlay position. The transition region may be configured to extend from the lateral portion along the spermatic cord and through the transversalis fascia to the medial portion with a segment of transition region being located within the thickness of the transversalis fascia. The prosthesis may be particularly configured for mending a groin hernia using the ONSTEP procedure The transition region may be configured to inhibit buckling and/or bunching of the patch that could otherwise potentially occur due to placement of the transition region through the transversalis fascia. For example, the transition region may be configured to inhibit squeezing or pinching by the transversalis fascia and/or other anatomical features to an extent that could otherwise cause the patch material to buckle and/or bunch. For purposes of this application, the term "inhibit" includes restrain, reduce, limit, minimize, avoid and/or prevent.

The patch may be configured to have sufficient stiffness or rigidity so that it can be easily and effectively manipulated and positioned in a desired anatomical region, yet have sufficient flexibility or compliance so that the patch may be adequately handled by the physician implanting the patch. The balance of stiffness and flexibility may facilitate deployment and implantation of portions of the patch in different tissue planes while inhibiting one or more undesirable consequences that could potentially occur from implantation of the patch. For example, and without limitation, the patch may be configured to inhibit patient sensation such that the implanted patch may be tolerated by the patient. In one embodiment, the lateral portion of the patch may be configured with a level of stiffness that facilitates implantation of the patch in different tissue planes while inhibiting patient sensation to the implanted patch.

The prosthesis may include a member, such as a support member, that may be arranged in or on the repair fabric. The support member may provide a desired level of stiffness or rigidity that helps deploy and/or hold the body portion in an open or spread out configuration for mending the defect. The support member may also provide a desired level of resiliency or compliance that facilitates manipulating the body portion and allows the support member to deform from an initial shape and then return to the initial shape to return the body portion of the patch to the spread out configuration. The support member, alone or together with the repair fabric, may also provide a desired level of flexibility or compliance that permits the prosthesis to be flexed and implanted in different tissue planes while inhibiting patient sensation from the implanted prosthesis.

The support member may be configured to extend along the medial portion, the transition region and the lateral portion. One or more segments of the support member extending along the transition region may be configured to inhibit being squeezed or pinched when positioned through tissue and/or muscle, such as the transversalis fascia, separating tissue planes so as to inhibit buckling or bunching the implanted patch. In one embodiment, the portion of the support member extending along the transition region may have an outer width that does not exceed the size of the incision, dissection or other opening created through the tissue and/or muscle. A portion of the support member extending along the medial portion of the patch may be wider than the portion of the support member along the transition region and larger than the size of the opening through the tissue and/or muscle. A portion of the support member extending along the lateral portion of the patch may be narrower than along the transition region.

The support member may be configured to substantially surround the body portion, such as in a ring-like manner, to help deploy and/or hold the body portion in an open or spread out configuration. The support member may be configured to generally follow the shape of the outer periphery of the repair fabric about the body portion. One or more segments of the support member may deviate inwardly away from the outer periphery toward the body portion to inhibit contact with adjacent anatomical features that may be present during a repair procedure. The inwardly directed segments of the support member may form one or more indentations or notches. A portion of the repair fabric may extend across each indentation or notch between the support member and the outer periphery. Alternatively, the prosthesis may be configured with the outer periphery of the repair fabric following the shape of the support member so that each indentation or notch is substantially free of repair fabric material.

The support member may include a pair of indentations or notches to accommodate a particular repair procedure and/or anatomical feature at the repair site. For example, and without limitation, the indentations may be located along the transition region of the repair fabric to form at least a portion of a transition segment of the support member with a reduced outer width for placement through tissue and/or muscle separating tissue planes. This configuration may inhibit inwardly directed radial forces being exerted against the support member by adjacent tissue and/or muscle, as well as other anatomical features, which could potentially squeeze or pinch the support member inwardly and cause undesirable buckling and/or bunching of the implanted patch.

The support member may include first and second ends that are spaced apart to form an interruption. In this manner, a slit, such as a keyhole arrangement, may be readily formed in the repair fabric through the interruption and into an interior region of the body portion. The slit and/or keyhole may be configured to receive a body structure, including a cord structure such as the spermatic cord. It is to be understood, however, that the support member may be configured to completely surround the body portion and not include an interruption.

For a procedure that may involve receiving a body structure, such as a spermatic cord, through an interruption and the repair fabric, the support member may be configured with segments extending along the transition region that are spaced apart a sufficient amount to accommodate the body structure therebetween. In one embodiment, the segments of the support member may have an inner width therebetween that permits the body structure to be received along the transition region.

The prosthesis may have a non-circular shape, such as a generally oval, elliptical or egg shape, which is suitable for mending a groin hernia. The prosthesis may be shaped so as to have a major axis and a minor axis. The support member may include a relatively narrow transition segment, formed at least in part by indentations or notches that are offset to one side of the minor axis toward a lateral end of the prosthesis, for inhibiting potential squeezing or pinching of the support member when implanting the patch through an opening in the tissue and/or muscle, such as the transversalis fascia, separating the tissue planes. The support member may include an interruption located on the major axis at the lateral end of the patch. The prosthesis may be generally symmetric about its major axis and generally asymmetric about its minor axis.

The support member may be rollable, foldable or otherwise collapsible, when the repair fabric is reduced in size for delivery to the repair site, and may spring back, either automatically or upon the influence of a force (e.g., body heat where the support is formed of a shape memory material, such as NITINOL) to its initial expanded shape on deployment at the repair site, influencing the prosthesis to assume its unfurled or spread out configuration.

The support member may be formed of a monofilament that has been preformed into the desired shape. The support member may be comprised of a resorbable or a non-resorbable material. In one embodiment, the support member is formed of a resorbable material to provide short-term support along an implanted patch. A resorbable support member also eliminates potential long-term sensation that could otherwise be experienced by a patient from use of the support member.

The prosthesis may include one or more positioning tethers, such as straps, to facilitate placement and fixation of the patch. A tether may be positioned on the patch in an off-center location. The center of the tether may be offset from the center of the patch in a direction toward the lateral end of the patch along the major axis. Such an arrangement may be particularly suited for a preperitoneal inguinal hernia repair performed though an open, anterior approach. The tether may be configured with a length that is sufficient to be accessible from outside a patient to facilitate placement, positioning and fixation of the patch.

The repair fabric may be formed of a tissue infiltratable material, such as a knit fabric, or may be composed of a solid or substantially non-porous material. The repair fabric may be formed of one or more layers of the same or dissimilar material. The repair fabric may be formed with portions that are tissue infiltratable and other portions that are non-tissue infiltratable, providing selected areas of the repair device with different tissue ingrowth and adhesion resistant properties. The repair fabric may be formed of permanent or resorbable material.

Figure 1:
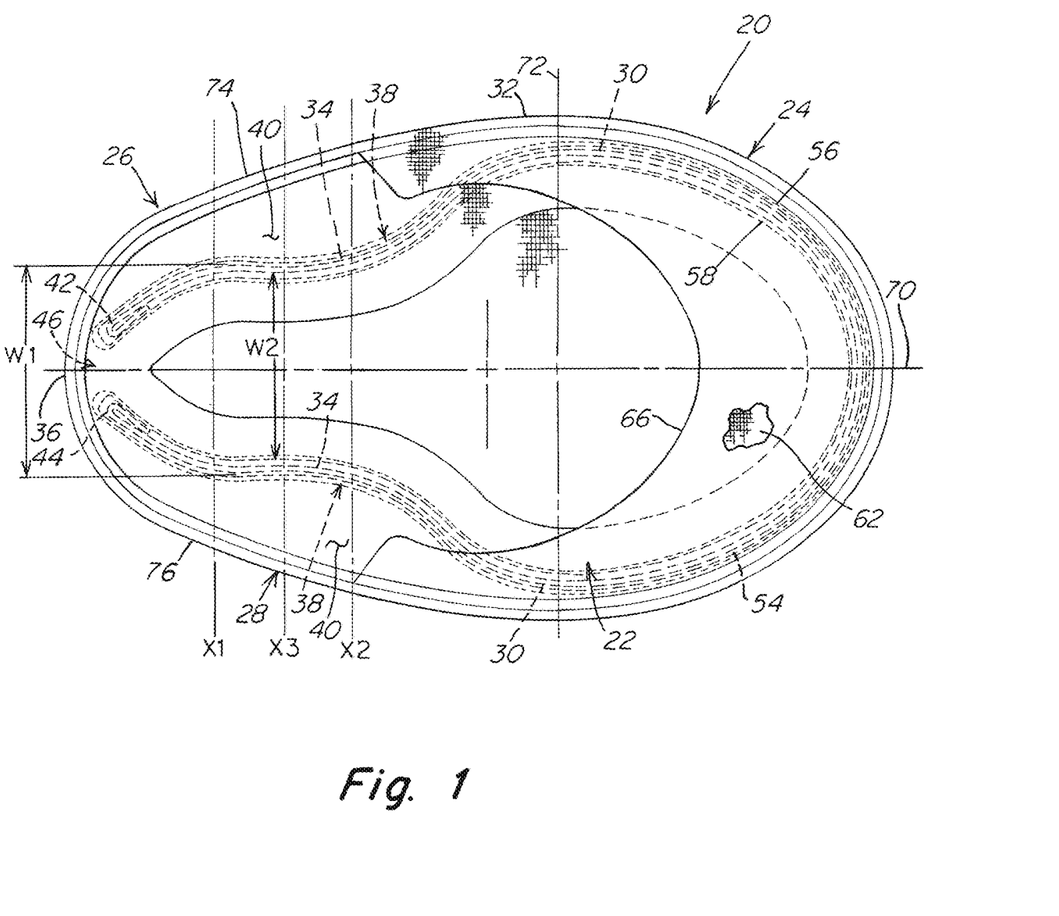
FIG. 1 is a plan view of an implantable prosthesis for mending an anatomical defect according to one illustrative embodiment.
Figure 2:
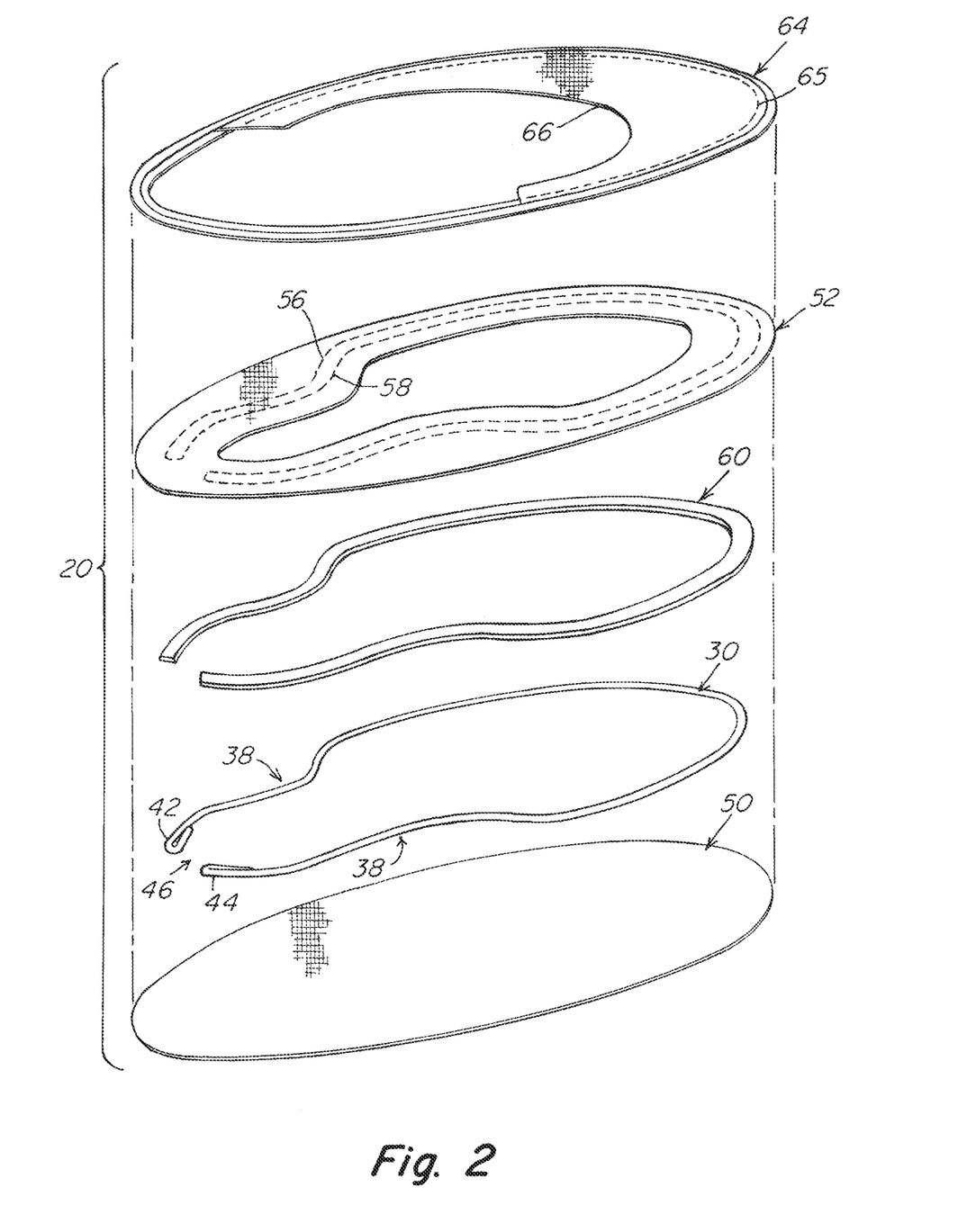
FIG. 2 is an exploded perspective view of the implantable prosthesis of FIG. 1.

FIGS. 1-2 illustrate one embodiment of a prosthesis 20 for mending soft tissue and muscle wall defects, such as a groin defect.

The prosthesis 20 includes a repair fabric of implantable, biologically compatible material with a body portion 22 that is configured to be positioned in one or more tissue planes to mend the defect. As shown, the prosthesis is configured as a patch that includes a medial portion 24 and a lateral portion 26 which are positionable in the same tissue plane or different tissue planes that are separated from each other by tissue and/or muscle. The patch also includes a transition region 28 which is configured to pass through the tissue and/or muscle separating the tissue planes when the prosthesis is employed for a multi-plane procedure. In one embodiment, the transition region extends along the lateral portion of the patch. The transition region may also extend along the medial portion of the patch. Alternatively or additionally, the transition region may extend along a portion of the patch between the medial and lateral portions.

The prosthesis may be configured with any desired characteristic or combination of characteristics including, but not limited to, strength, stiffness, flexibility, tissue integration and/or adhesion resistance, suitable for the repair as should be apparent to one of skill. Although the prosthesis is described in connection with a patch-type embodiment, the prosthesis may include a plug, a combination plug and patch, and other suitable arrangements for mending the defect.

To help deploy the patch into a spread out configuration for mending a defect, it may be desirable to employ a patch that is sufficiently rigid so that it can be easily and effectively manipulated and positioned in a desired anatomical region, yet sufficiently flexible so that the patch may be adequately handled by the physician implanting the patch and tolerated by the patient receiving the patch. A desired stiffness, flexibility or compliance may be provided to the patch using suitable components, features, materials, coatings and/or treatments as should apparent to one of skill in the art.

In one illustrative embodiment as shown in FIGS. 1-2, to balance the stiffness and flexibility characteristics, the prosthesis 20 includes a support member 30 to reinforce portions of the patch and to help deploy and/or hold the patch in a spread out configuration. The support member 30 may be coupled to the patch in any suitable manner, as the present invention is not limited in this respect. Suitable attachment methods include, but are not limited to, stitching, bonding, adhesive, and integral formation with the repair fabric of the patch, as should be apparent to one of skill.

The support member 30 contributes to the stability of the patch, allowing it to deploy into and remain in a desired shape. For example, the support member may aid in returning the patch to a substantially unfurled or spread out configuration after the folded up or otherwise reduced prosthesis has been delivered to the repair site through either an open incision or a cannula. This stability facilitates deployment and placement of the patch by making it easy to handle. Also, this stability minimizes the tendency of the patch to fold, bend, or otherwise be dislocated.

In one embodiment, the support member 30 includes a substantially continuous loop or ring positioned adjacent the outer margin of the patch. In the illustrative embodiment, the support member 30 is spaced inwardly from the outer peripheral edge 32 of the repair fabric. However, it should be appreciated that the present invention is not limited in this respect, as the support member 30 may be disposed at the peripheral edge and/or at discrete locations throughout the body of the patch.

The support member 30 may be configured to substantially surround the body portion so as to help deploy and/or hold the body portion 22 in the spread out configuration for covering the defect. The support member 30 may have a resiliency that allows the support member to deform from an initial shape and then return to the initial shape to return the body portion to the spread out configuration.

In certain repair procedures, it may be desirable to configure the support member in a manner that inhibits the application of undesirable forces between the support member and adjacent anatomy at the repair site. In one embodiment, the support member may be configured so as to inhibit inwardly directed deflection by the adjacent anatomy. For example, pinching or squeezing the support member inwardly could potentially cause buckling and/or bunching of the repair fabric which could adversely impact repair of the defect with the prosthesis.

In one illustrative embodiment shown in FIGS. 1-2, the support member 30 may be configured with a transition segment 34 along the transition region of the patch that permits the patch to be positioned within an incision or dissected tissue and/or muscle without causing the support member to be deflected or squeezed inwardly by adjacent anatomy. The transition segment 34 may be configured with an outer width $W_1$ that does not exceed the size of the incision, dissection or other opening created or otherwise present through the tissue and/or muscle separating the tissue planes. The transition segment may extend along a region of the patch located from a first distance $X_1$ to a second distance $X_2$ relative to the lateral end of the patch.

In one embodiment, the outer width $W_1$ of the transition segment of the support member does not exceed 4.2 cm along a region $X_1$-$X_2$ of the patch located approximately 1 inch (2.5 cm) ($X_1$) to approximately 2 inches (5.1 cm) ($X_2$) from the lateral end 36 of the patch. The outer width $W_1$ of the transition segment along the region $X_1$-$X_2$ may range from 2.5 cm to 4 cm. In another embodiment, the outer width $W_1$ of the transition segment of the support member does not exceed 3.7 cm along a region of the patch located approximately 1 inch (2.5 cm) ($X_1$) to approximately 1.5 inches (3.8 cm) ($X_3$) from the lateral end 36 of the patch. The outer width $W_1$ of the transition segment of the support member may range from 2.5 cm to 3.5 cm along the region $X_1$-$X_3$ of the patch. A patch including a support member with a transition segment configured in this manner may be particularly suited for mending a groin hernia using the ONSTEP procedure. However, it is to be appreciated that the support member may be provided with a transition segment having other configurations suitable for other procedures as should be apparent to one of skill.

As shown, the support member 30 may deviate inwardly away from the outer periphery 32 of the patch to form a pair of indentations or notches 38. The support member 30 may have a generally convex curvature as it extends about the medial portion 24 while the indentations 38 may have a generally concave curvature extending from the medial portion 24 along the transition region 28 toward the lateral portion 26. As illustrated, segments of the support member extending from the indentations toward the lateral end of the patch may have a generally convex curvature. A portion of the support member along the lateral portion of the patch may be narrower than the transition segment, and a portion of the support member along the medial portion of the patch may be wider than the transition segment.

In the illustrative embodiment shown in FIG. 1, segments of repair fabric may occupy the regions of the patch at the indentations 38 between the support member 30 and the outer periphery 32. For example, the fabric segments 40 may enhance tissue ingrowth about the portion of the patch, such as the transition region, extending through tissue and/or muscle separating tissue planes involved with the defect repair. If desired, the fabric segments may be trimmed to accommodate the particular anatomy.

As illustrated in FIGS. 1-2, the support member 30 may include first and second ends 42, 44 that are spaced apart to form an interruption 46 in the support member at an end of the prosthesis. In this manner, a slit and/or keyhole arrangement may be formed in the repair fabric at the interruption 46 and into an interior region of the body portion 22 without having to cut through the support member. The slit and/or opening may be configured to receive a body structure, including a cord structure such as the spermatic cord. It is to be understood, however, that the support member in some embodiments may be configured to completely surround the body portion and not include an interruption.

For a procedure that may involve receiving a body structure, such as a spermatic cord, through an interruption and the repair fabric, the support member 30 may be configured with transition segments 34 extending along the transition region that are spaced apart a sufficient amount to accommodate the body structure therebetween. For example, the segments 34 of the support member may have a minimum width $W_2$ therebetween that permits the body structure to be received along the transition region. In one embodiment, the support member may have a minimum width $W_2$ of about 2.4 cm for receiving a spermatic cord therebetween, such as when mending a groin hernia, although other configurations may be implemented as should be apparent to one of skill.

The support member 30 may be integrated with the patch in any suitable manner as the present invention is not limited in this respect. In one embodiment, as shown in FIGS. 1-2, the support member 30 is sandwiched between first and second layers 50, 52 of repair fabric and may or may not be physically attached thereto. The support member 30 may be held within a channel 54 between the first and second layers. In the illustrative embodiment, the channel 54 is formed by a pair of seams 56, 58 that join the first and second layers and follow the contour of the support member 30. The seams may be formed by a series of stitches, or other suitable arrangements, extending along the outside and inside edge of the support member 30 to keep it from moving with respect to the first and second layers. In some embodiments, one seam extending along one side of the support member may be sufficient.

It should be appreciated that the invention is not limited to any particular attachment method, as the first and second layers 50, 52 may be attached along the seams 56, 58 or other desired locations using other suitable techniques. For example, the layers may be bonded together by melting the layers at specific locations or in a specific pattern; sonic, induction, vibration, or infrared/laser welding the layers; or using a suitable bonding agent. The point or points of attachment may comprise any suitable pattern as would be apparent to one of skill in the art.

In one embodiment as shown in FIG. 2, the support member may be surrounded by a containment sleeve 60 that is located between the first and second layers. A containment sleeve may be particularly advantageous when used in conjunction with a resorbable support member. The sleeve may be formed from a mesh fabric that includes interstices or pores that allow tissue infiltration or ingrowth that eventually surrounds and resorbs the support member 30. However, it should be understood that a containment sleeve is not required for each embodiment of the invention, including embodiments that employ a resorbable support member.

In one illustrative embodiment shown in FIGS. 1-2, the first layer 50 may be configured as a full layer of fabric material that is sized and shaped to cover the defect. The second layer 52 may have a generally annular configuration that overlies and generally follows the contour of the support member to reduce the overall amount of material for the prosthesis. However, it is to be appreciated that the second layer 52 may have any suitable configuration as should be apparent to tone of skill in the art.

For some repair procedures, it may be desirable to provide one or more pockets that may aid in deploying and/or positioning of the prosthesis during implantation as should be understood by one of skill in the art. The pocket may be configured to receive a sufficient length of one or more fingers of an individual's hand (or a suitable surgical instrument) for deploying and/or placing the prosthesis.

In one embodiment shown in FIGS. 1-2, the prosthesis may include a pocket 62 located at an end of the medial portion of the patch. The pocket 62 may be created with a layer 64 of fabric that is attached to the body portion in a manner that forms the pocket therebetween. As shown in FIG. 2, the pocket layer 64 may be attached to the body portion along a seam 65, such as a stitch line, that is located outside the support member 30 and adjacent the outer periphery of the of the patch. This arrangement may facilitate placement of the patch by providing a pocket that extends close to the edge of the patch which may allow a user to more readily recognize the position of the outer edge through tactile feedback during implantation. An opening may be provided for permitting access of an individual's fingers (or surgical instrument) therethrough and into the pocket. The opening may be located along an edge 66 of the layer of fabric. However, the pocket may employ any suitable configuration and/or may be located at any suitable portion of the prosthesis as should be apparent to one of skill in the art. If desired, one or more additional pockets, such as a pocket located at the lateral portion 26, may be provided on the prosthesis.

As indicated above, the patch may be configured with a desired level of stiffness, flexibility or compliance in one or more regions that helps deploy and/or hold the body portion in an open or spread out configuration for mending the defect, facilitates manipulating the body portion and/or permits the prosthesis to be flexed and implanted in different tissue planes while minimizing patient sensation from the implanted prosthesis.

In one embodiment, the lateral portion 26 of the patch may be configured with a level of stiffness that facilitates implantation of the patch in different tissue planes while inhibiting patient sensation to the implanted patch. For purposes of this application, the stiffness of the lateral portion is determined following the test procedure described below using the test fixture illustrated in FIG. 6. In one embodiment, the patch may be configured with a lateral portion that has a stiffness of 0.04 psi to 0.09 psi. In another embodiment, the lateral portion may have a stiffness of 0.04 psi to 0.07 psi. In another embodiment, the lateral portion may have a stiffness of 0.04 psi to 0.06 psi. In another embodiment, the lateral portion may have a stiffness of 0.05 psi to 0.09 psi. In another embodiment, the lateral portion may have a stiffness of 0.05 psi to 0.07 psi. It is to be appreciated, however, that the patch may be configured with the lateral portion or other portions having other stiffnesses as should be apparent to one of skill.

The prosthesis may be configured to have any suitable shape or size that is conducive to facilitate mending of a particular defect, such as a groin hernia. In the embodiments shown in FIGS. 1-2, the patch has a relatively flat configuration. However, the patch need not be flat, and convex, concave, convex/concave, and more complex three-dimensional shapes also are contemplated. The patch may be sufficiently pliable to facilitate manipulation and/or reduction of the patch during delivery to the defect and/or to conform the patch to the anatomical site of interest.

In the illustrative embodiments shown in FIGS. 1-2, the prosthesis has a generally oval, elliptical or egg shape suitable for mending a groin hernia in the inguinal canal. The geometry of the prosthesis 20 is generally oval with a major axis 70 extending along the longest portion of the prosthesis and a minor axis 72 extending across the widest portion of the prosthesis in a direction perpendicular to the major axis. As illustrated in FIG. 1, the prosthesis is substantially symmetric about the major axis 70 and is substantially asymmetric about the minor axis 72 providing a generally ovoid shape (e.g., egg shape) with a narrower lateral portion 26, a wider medial portion 24, and opposing sides 74, 76 that converge towards each other in a direction from the medial portion 24 toward the lateral portion 26. It is to be appreciated that the prosthesis may be configured with any suitable shape, such as a shape that is symmetric about both axes, asymmetric about both axes, or asymmetric about the major axis and symmetric about the minor axis. Examples of other shapes include, but are not limited to, circular, square, rectangular, and irregular configurations. The repair fabric may be sized to cover part or, preferably, all of the defect.

The medial portion 24 has a rounded configuration that generally conforms to the shape of the repair site, for example, a preperitoneal space, such as the space of Retzius. The medial portion of the prosthesis has a relatively larger configuration or size to provide more potential coverage at the defect site. The lateral portion 26 of the prosthesis may have a smaller, less rounded configuration relative to the medial portion which may be conducive for positioning in a separate tissue plane, such as an onlay position, for example, between an external oblique aponeurosis and an internal oblique aponeurosis. However, it is to be understood that the medial and lateral portions may have any suitable configurations apparent to one of skill in the art.

The transition region 28 and the interruption 46 may be positioned in any desirable location, relative to the body portion 22, which is suitable for a particular repair. In the illustrative embodiment, the transition region 28 is offset from the minor axis 72 toward the lateral portion 26 of the prosthesis. The interruption 46 is centrally located along the major axis 70 at the lateral portion 26 of the prosthesis. As shown, the transition region 28 may be located entirely to one side of the minor axis toward the lateral portion. The illustrated embodiments of the interruption and the transition region are particularly suited for mending a groin hernia. However, it is to be appreciated that the prosthesis is not so limited and the locations of the interruption and/or the transition region may be varied for other repairs as would be apparent to one of skill in the art.

For certain procedures, it may be desirable to employ one or more positioning tethers to facilitate placement and fixation of the patch. In one illustrative embodiment shown in FIGS. 3-4, the prosthesis may include a patch 20 and a tether 80, such as a strap, extending from the patch. In this embodiment, the patch generally corresponds to the embodiment described above with reference to FIGS. 1-2, such that details of the patch will not be described in connection with this embodiment. However, the prosthesis may include a pocket 62a, 62b at both the medial and lateral portions of the patch. As illustrated, the pocket layer 64 may be configured to form the pockets in conjunction with the body portion of the patch.

Figure 3:
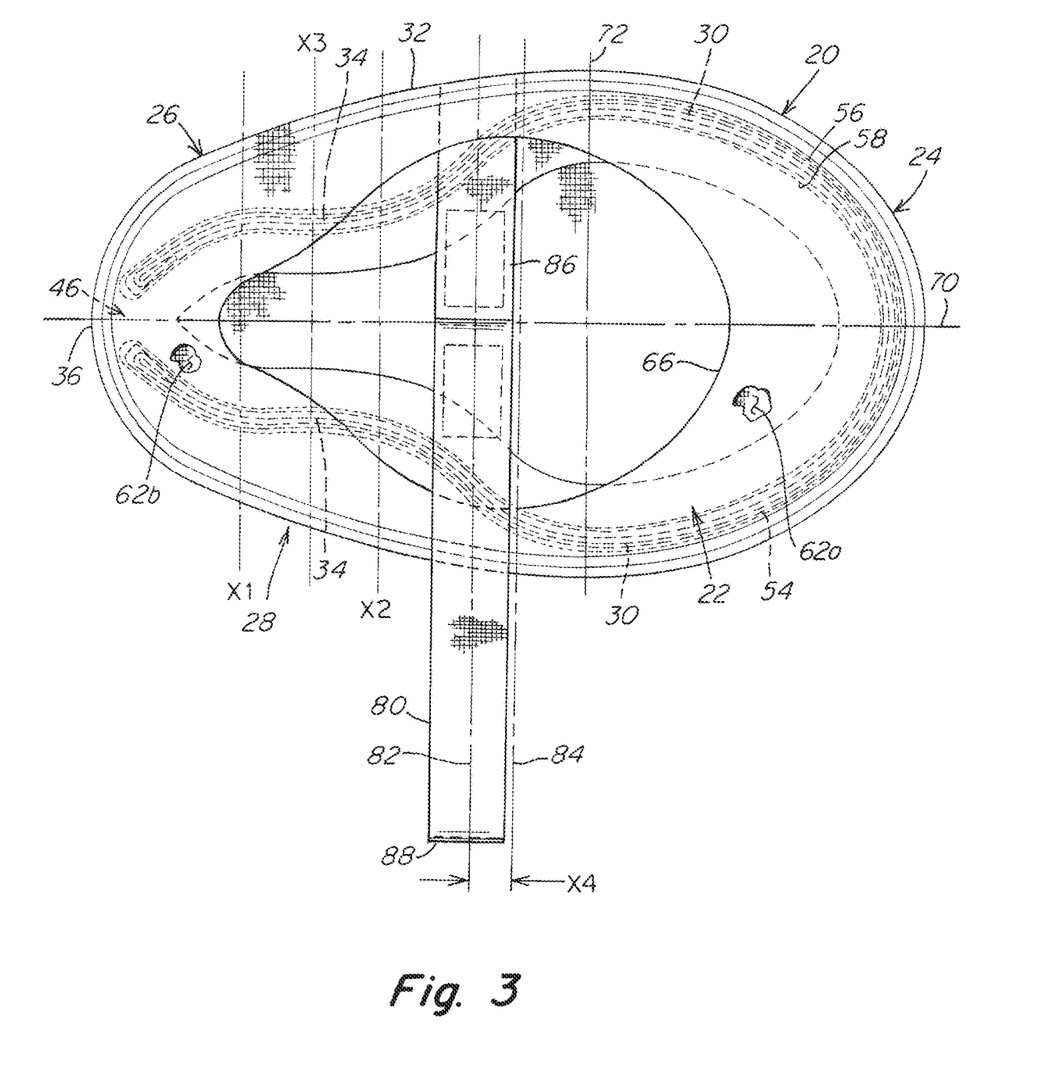
FIG. 3 is a plan view of an implantable prosthesis for soft tissue repair according to another illustrative embodiment.
Figure 4:
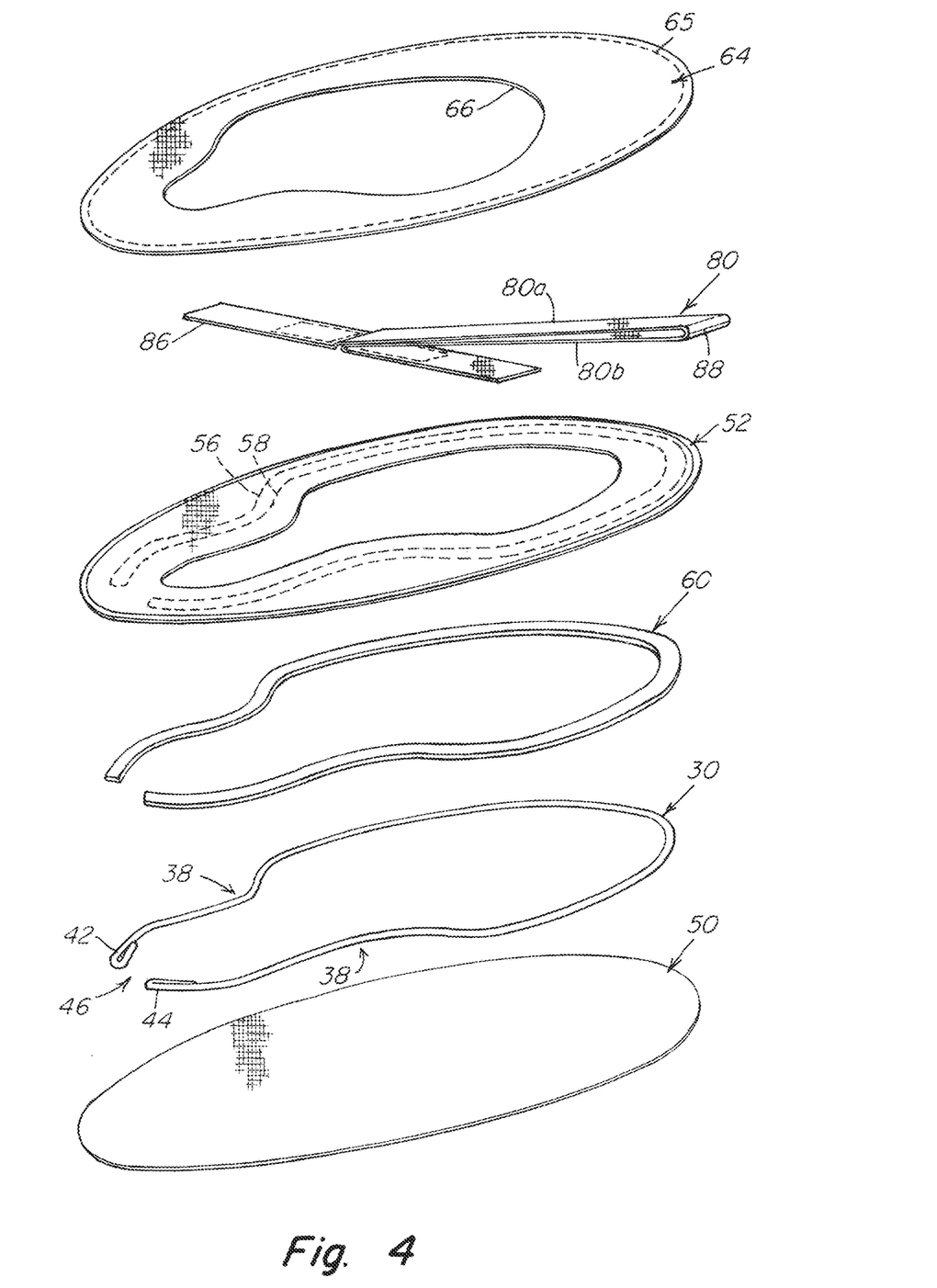
FIG. 4 is an exploded perspective view of the implantable prosthesis of FIG. 3.

In one embodiment, the tether 80 may be positioned on the patch in an off-center location. As shown, the center 82 of the tether 80 may be offset from the center 84 of the patch in a direction toward the lateral end of the patch along the major axis. The off-center location of the tether allows the patch to be fixated through either an indirect hernia or a direct hernia while still providing desired coverage of the defect spaces. Such an arrangement may be particularly suited for a preperitoneal inguinal hernia repair performed through an open, anterior approach. The tether may be configured with a length that is sufficient to be accessible from outside a patient to facilitate placement, positioning and fixation of the patch.

The tether 80 may include a base 86 that is secured, such as by stitching, to the patch. As shown, the base 86 may be located between the second layer 52 and a pocket layer 64, if provided. In one embodiment, the tether includes a pair of straps 80a, 80b that extend from the base and are joined together with a looped end 88. The base may include separate bases at the end of each strap. It is to be appreciated, however, that other arrangements are contemplated as should be apparent to one of skill.

In one embodiment, the tether may be formed from a repair fabric, such as a mesh fabric similar to material employed for other layers of the patch. The tether may have a width of approximately 0.5 inches and a length of approximately 3.8 inches. The tether may be offset from the center of the patch toward the lateral end by a distance $X_4$ of 0.25 inches. However, the strap may be formed of any suitable material, have any suitable configuration and be located in any suitable position as should be apparent to one of skill.

In one embodiment for a mending a groin hernia, the patch 20 has a length along the major axis 60 of approximately 5.6 inches and a width along the minor axis 62 of approximately 3.4 inches. In another embodiment for mending a groin hernia, the patch 20 has a length along the major axis 60 of approximately 6.2 inches and a width along the minor axis 62 of approximately 4.0 inches. Each patch may employ a support member having a transition segment with a configuration as described above. The interruption may have a width from approximately 0.5 cm to approximately 4.0 cm. However, it is to be understood that these dimensions are merely exemplary and that the prosthesis may be configured to have any suitable size and interruption width as would be apparent to one of skill for a particular repair.

The repair fabric may include at least one layer of tissue infiltratable material that permits or is otherwise susceptible to tissue or muscle ingrowth to enhance the repair of the defect. In one embodiment, each layer 50, 52, 64 is formed of a biologically compatible, flexible repair material that includes a plurality of interstices or openings which allow sufficient tissue or muscle ingrowth to integrate the prosthesis with host tissue or muscle after implantation. Multiple layers of tissue infiltratable fabric may enhance the strength of the patch and/or the amount of tissue ingrowth to the patch. However, the invention is not limited in this respect, and any one or each layer may be formed of any biologically compatible material, suitable for repairing a tissue or muscle wall defect as would be apparent to one of skill.

In one embodiment, the layers 50, 52, 64 of the prosthesis 20 are each formed from a sheet of knitted polypropylene monofilament mesh fabric having a thickness of approximately 0.016 inches and knitted from polypropylene monofilament having a diameter of approximately 0.0043 inches. The tether 80, if employed, may be formed of similar mesh fabric.

When implanted, the polypropylene mesh promotes rapid tissue or muscle ingrowth into and around the mesh structure. Alternatively, other surgical materials which are suitable for tissue or muscle reinforcement and defect correction may be utilized including BARD MESH (available from C.R. Bard, Inc.), SOFT TISSUE PATCH (microporous ePTFE—available from W.L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Resorbable materials, including polyglactin (VICRYL—available from Ethicon, Inc.) and polyglycolic acid (DEXON—available from US Surgical, Inc.), may be suitable for applications involving temporary correction of tissue or muscle defects. Collagen materials such as COOK SURGISIS, available from Cook Biomedical, Inc. may also be used. It also is contemplated that the mesh fabric may be formed from multifilament yarns and that any suitable method, such as knitting, weaving, braiding, molding and the like, may be employed to form the mesh material.

In one embodiment, the support member may be formed from a length of 0.038 inch diameter resorbable polydioxanone (PDO) monofilament. In this manner, the support member provides a desired level of support for initial placement and positioning of the prosthesis. However, it should be appreciated that the invention is not limited in this respect and that the support member may be made of any suitable resorbable and non-resorbable material including, but not limited to, a resorbable PLA/PCL blend or non-resorbable materials, such as polyethylene terephthalate (PET) nylon, polypropylene, and polyester, and having any suitable diameter or cross-section. If desired, the stiffness or rigidity of the support member may be varied depending on the size of the patch. For example, the cross-sectional diameter and/or the spring constant of the material of the monofilament may be varied in a manner to provide a desired stiffness throughout or in one or more portions of the prosthesis.

In certain embodiments, the prosthesis may include an adhesion resistant barrier overlying at least a portion, and preferably all, of one side of the ingrowth layer and/or an edge barrier to isolate one or more edges of the patch from adjacent tissue, muscle or organs. The barrier layer and/or edge barrier may be formed of a material and/or with a structure that does not substantially stimulate and, in certain embodiments, may resist tissue, muscle or organ ingrowth and adhesion formation when implanted, thereby reducing the incidence of undesired postoperative adhesions between the ingrowth layer and adjacent tissue, muscle or organs. If desired, such a barrier layer and/or edge barrier may be formed from any suitable material or structure apparent to one of skill in the art, including, but not limited to, a sheet of expanded polytetrafluoroethylene (ePTFE) having a microporous pore structure that inhibits tissue ingrowth.

In certain embodiments, the prosthesis may be loaded with one or more medicinal or therapeutic agents including, but not limited to, an analgesic or antibiotic.

Figure 5:
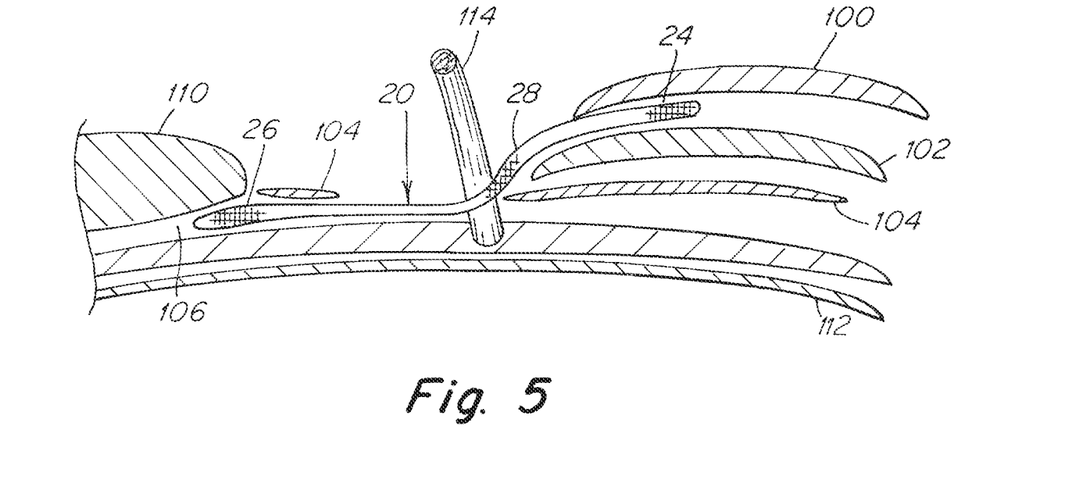
FIG. 5 is a schematic illustration of the prosthesis of FIGS. 1-2 being implanted to mend a groin hernia.

As indicated above, the prosthesis 20 illustrated in FIGS. 1-2 may be particularly suited for mending a groin hernia using the ONSTEP procedure. As illustrated in FIG. 5, the procedure involves creating a space between the external oblique aponeurosis 100 and the internal oblique aponeurosis 102 superiorly and laterally to an incision site. This space may be configured to receive a lateral portion of a prosthetic repair patch. Medially and inferiorly of the dissected space between the two oblique aponeuroses, and remote from the groin defect, the transversalis fascia 104 is penetrated to reach the space of Retzius 106—an area located deep of the pubic bone 110 and anteriorly of the peritoneum 112. A surgically created pathway now runs from the space of Retzius 106, a preperitoneal space, to the dissected area between the external oblique aponeurosis 100 and the internal oblique aponeurosis 102.

A patch 20 is implanted along this pathway, with the lateral portion 26 positioned in the dissected space between the external oblique aponeurosis and the internal oblique aponeurosis and the medial portion 24 extending through the transversalis fascia to the preperitoneal area of the pubic bone 110. A transition region 28 runs with the spermatic cord 114, extending transversely between the medial and lateral portions of the prosthetic repair patch. A slit may be provided in the lateral portion to define two separable portions, referred to as "tails", which may be spread apart to accommodate the spermatic cord. Subsequently, the tails are reunited and, if desired, sutured together or otherwise secured.

Examples

The following examples are illustrative only and are not intended to limit the scope of the present invention.

The stiffness of an implantable prosthesis, similar to the patch illustrated in FIGS. 1-2, was tested and the resulting data is presented in Table 1 below. More particularly, the stiffness was tested for the lateral portion of the patch. For a groin hernia repair, such as using the ONSTEP procedure, the lateral portion may be implanted anteriorly to the transversalis fascia in an onlay position.

Figure 6:
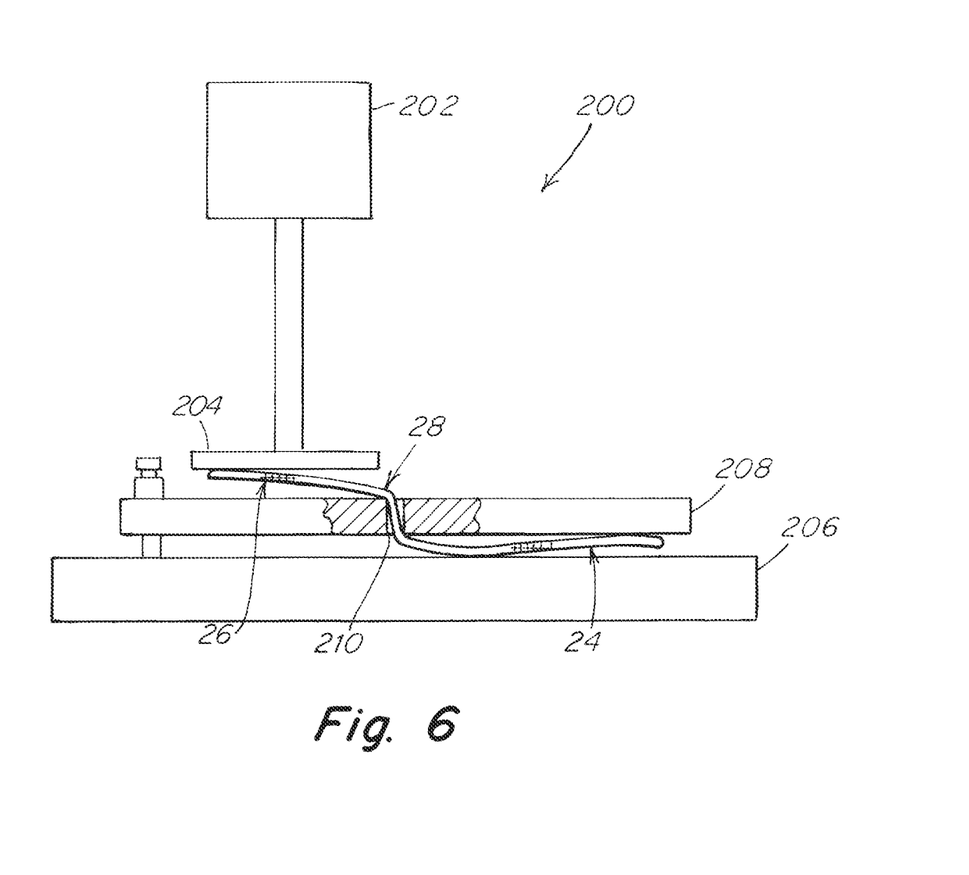
FIG. 6 is a schematic illustration of a test fixture for testing the stiffness of a portion of an implantable prosthesis.

FIG. 6 provides a schematic illustration of a test fixture 200 for testing stiffness of the prosthesis. An Instron tester 202 with a flat plate test probe 204 (measuring 2"×3") is used to determine the stiffness of the samples. The tester measures the force exerted by the patch against the probe to bend the lateral portion of the sample approximately 90°.

The medial portion 24 of the sample, approximately 3 to 3.6 inches depending on the size of the patch, is placed between a base plate 206 and a foam pad 208 which is secured to the base. Approximately 2 inches of the patch, corresponding to the lateral portion 26, extends from a slit 210 in the foam pad and is positioned below the test probe 204 extending generally in a direction along the horizontal plane of the pad. In this manner, the medial and lateral portions of the patch are placed in two different planes.

The test probe 204 is advanced in the downward vertical direction at a rate of 1 inch/min to deflect the lateral portion 26 of the patch downward toward the pad 208. The test probe 204 is advanced to a position approximately 0.13 inches above the foam pad. Peak force exerted by the patch against the probe was recorded.

Eighteen samples were tested, including 10 samples (N) of a medium patch (5.6"×3.4") and 8 samples (N) of a large patch (6.2"×4.0"). The lateral portions of the medium and large samples generally had the same configurations with a test area of about 4.55 in² (medium) and 4.56 in² (large). The average stiffness was calculated for the lateral portion. Stiffness data is provided in Table 1, measured in lbf/in² (psi).

TABLE 1

|  | Medium Patch | Large Patch |
| --- | --- | --- |
| Mean (psi) | 0.050 | 0.070 |
| Std. Dev. | 0.007 | 0.010 |
| N (Tested Samples) | 10 | 8 |
| Max. (psi) | 0.062 | 0.091 |
| Min. (psi) | 0.041 | 0.057 |

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. A method of mending a groin hernia, the method comprising acts of:
   (a) providing an implantable prosthesis that includes a patch of repair fabric and a support member to help deploy and/or hold the patch in a spread out configuration, the patch including a medial portion, a lateral portion and a transition region, the support member being located along the medial portion, the lateral portion and the transition region, the support member including a transition segment associated with the transition region; and
   (b) implanting the prosthesis to mend the groin hernia by:
      (i) positioning the medial portion of the patch at a first tissue plane;
      (ii) positioning the lateral portion of the patch at a second tissue plane offset from the first tissue plane; and
      (iii) positioning the transition region of the patch through an opening in tissue and/or muscle separating the first and second tissue planes, the transition segment of the support member having an outer width that does not exceed a corresponding dimension of the opening.

2. The method according to claim 1, wherein act (a) includes providing the prosthesis with the transition segment of the support member having an outer width that does not exceed 4.2 cm.

3. The method according to claim 2, wherein act (a) includes providing the prosthesis with the transition segment of the support member extending 2.5 cm to 5.1 cm from the lateral end of the patch.

4. The method according to claim 2, wherein act (a) includes providing the prosthesis with the transition segment of the support member having an outer width of 2.5 cm to 4.0 cm.

5. The method according to claim 4, wherein act (a) includes providing the prosthesis with the transition segment of the support member having an outer width of 2.5 cm to 3.5 cm.

6. The method according to claim 4, wherein the transition region extends in a longitudinal direction along the patch, act (a) includes providing the prosthesis with the transition segment of the support member having a length of 2.5 cm in the longitudinal direction.

7. The method according to claim 4, wherein the patch includes a lateral end, act (a) includes providing the prosthesis with the transition segment of the support member located at least 2.5 cm from the lateral end of the patch.

8. The method according to claim 4, wherein act (a) includes providing the prosthesis with the lateral portion having a stiffness of 0.04 psi to 0.09 psi.

9. The method according to claim 4, wherein act (a) includes providing the prosthesis with the lateral portion having a stiffness of 0.04 psi to 0.07 psi.

10. The method according to claim 4, wherein act (b)(i) includes positioning the medial portion in a preperitoneal space.

11. The method according to claim 10, wherein act (b)(i) includes positioning the medial portion in the space of Retzius.

12. The method according to claim 10, wherein act (b)(ii) includes positioning the lateral portion between an external oblique aponeurosis and an internal oblique aponeurosis.

13. The method according to claim 12, wherein act (b)(iii) includes positioning the transition segment of the support member through an opening in the transversalis fascia.

* * * * *